US006348316B1

(12) United States Patent
Taylor et al.

(10) Patent No.: US 6,348,316 B1
(45) Date of Patent: Feb. 19, 2002

(54) GENETIC TESTING FOR DETERMINING THE RISK OF POUCHITIS DEVELOPMENT

(75) Inventors: Kent D. Taylor, Santa Paula; Huiyang Yang, Cerritos; Jerome I. Rotter, Los Angeles; Phillip R. Fleshner, Beverly Hills, all of CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 09/556,868

(22) Filed: Apr. 12, 2000

(51) Int. Cl.[7] .......................... C12Q 1/68; C07H 21/02; C07H 21/04; C12N 15/00
(52) U.S. Cl. .................. 435/6; 536/23.1; 536/24.13; 935/76; 935/77; 935/78
(58) Field of Search ............................. 435/6; 536/23.1, 536/24.3; 935/76, 77, 78

(56) References Cited

U.S. PATENT DOCUMENTS

| 5,221,789 A |   | 6/1993 | Novick et al. |
| 5,937,862 A | * | 8/1999 | Targan et al. |
| 6,033,864 A | * | 3/2000 | Braun et al. |

FOREIGN PATENT DOCUMENTS

| WO | WO94/14467 | 7/1994 |
| WO | WO95/16036 | 6/1995 |
| WO | WO99/37682 | 7/1999 |

OTHER PUBLICATIONS

Facklis et al., Diseases of the Colon and Rectum 42 (5) : 601–605 (May 1999).*
Plevy et al., Gastroenterology 110(4) : 1053–1060 ( Abstract only—1996).*
Merlin et al., "The Gene for the Ligand Binding Chain of the Human Interferon Gamma Receptor," *Immunogenetics* 45:413–421 (1997).
Meagher et al., "J Ileal Pouch–anal Anastomosis for Chronic Ulcerative Colitis: Complications and Long–term Outcome in 1310 Patients," *British Journal of Surgery* 85:800–803 (1998).
Carter et al., "Association of the Allele 2 of the Interleukin–1 Receptor Antagonist Gene with Ulcerative Colitis Requiring Colectomy and Pouchitis," *Gut* 44 (4S):A50 (1999).
GenBank Accession No.: AL050337, Human DNA Sequence from clone 503F13.
GenBank Accession No.: J03143, Human Interferon Gamma Receptor mRNA, complete cds.
GenBank Accession No.: NM_005534, *Homo sapiens* interferon gamma receptor 2 mRNA.
GenBank Accession No.: U84721, *Homo sapiens* interferon gamma receptor 1 gene.

(List continued on next page.)

*Primary Examiner*—Ethan Whisenant
(74) *Attorney, Agent, or Firm*—Campbell & Flores LLP (57) ABSTRACT

The present invention provides a method of determining a risk of pouchitis development following a surgical procedure where an internal pouch is created in a patient with ulcerative colitis. The method is practiced by determining in the patient the presence or absence of a pouchitis-associated allele linked to an interferon γ receptor locus, where the presence of the pouchitis-associated allele indicates an increased risk of pouchitis development. The interferon γ receptor locus to which the pouchitis-associated allele is linked can be, for example, an interferon γ receptor 1 gene. A pouchitis-associated allele useful in the invention can be, for example, an allele located within the sixth intron of the interferon γ receptor 1 gene, such as a FA1 microsatellite 171 allele.

15 Claims, 3 Drawing Sheets

OTHER PUBLICATIONS

Aitola et al., "Chronic inflammatory changes in the pouch mucosa are associated with cholangitis found on peroperative liver biopsy specimens at restorative protocolectomy for ulcerative colitits," *Scan. J. Gastroenterol.* 33:289–293 (1998).

Altare et al., "A causative relationship between mutant IFNgR1 alleles and impaired cellular response to IFNγ in a compound heterozygous child," *Am. J. Hum. Genet.* 62:723–726 (1998).

Aparicio–Pages et al., "In vitro cellular cytotoxicity in Crohn's disease and ulcerative colitis: Relation with disease activity and treatment, and the effect of recombinant gamma–interferon," *J. Clin. Lab. Immunol.* 29:119–124 (1989).

Binder, "Pouchitis—Predictable by immunological or genetic markers?" *Eur. J. Gasteroent. & Hepatol.*, 8:943–945 (1996).

Bode et al., "IL–1β and TNF–α, but not IFN–α, IFN–γ, IL–6 or IL–8, are secretory mediators in human distal colon," *Cytokine* 10:457–465 (1998).

Brett et al., "Genetic and immunological markers in pouchitis," *Eur. J. Gastroenterol. Hepatol.* 8:951–955 (1996).

Camoglio et al., "Altered expression of interferon–γ and interleukin–4 in inflammatory bowel disease," *Inflamm. Bowel Dis.* 4:285–290 (1998).

Dib et al., "A comprehensive genetic map of the human genome based on 5,264 microsatellites," *Nature* 380:152–154 (1996).

Dumonceau et al., "Detection of fastidious mycobacteria in human intestines by the polymerase chain reaction," *Eur. J. Clin. Microbiol. Infect. Dis.* 16:258–363 (1997).

Facklis et al., "Crohn's disease–associated genetic marker is seen in medically unresponsive ulcerative colitis patients and may be associated with pouch–specific complications," *Dis. Colon Rectum* 42:601–605 (1999).

Fleshner et al., "Chronic Pouchitis After Ileal Pouch–Anal Anastomosis for Ulcerative Colitis (UC) is Associated with the Interferon–γ Receptor–α (IFNγRα) Gene Independent of Perinuclear Antineutrophil Cytoplasmic Antibody (pANCA) Level," Abstract from the DDW 2000 Conference in San Diego California, May 21–24, 2000.

Fuss et al., "Disparate CD4+ lamina propria (LP) lymphokine secretion profiles in inflammatory bowel disease. Crohn's disease LP cells manifest increased secretion of IFN–γ, whereas ulcerative colitis LP cells manifest increased secretion of IL–5," *J. Immunol.* 157:1261–1270 (1996).

Goldstein et al., "Crohn's–like complications in patients with ulcerative colitis after total proctocolectomy and ileal pouch–anal anastomosis," *Am. J. Surg. Pathol.* 21:1343–1353 (1997).

Hampe et al., "The interferon–γ gene as a positional and functional candidate gene for inflammatory bowel disease," *Int. J. Colorectal Dis.* 13:260–263 (1998).

Hanauer et al., "Inflammatory Bowel Disease," *New Eng. J. Med.*, 334:841–848 (1996).

Jouanguy et al., "A human IFNGR1 small deletion hotspot associated with dominant susceptibility to mycobacterial infection," *Nature Genet.* 21:370–378 (1999).

Jouanguy et al., "Interferon–γ–receptor deficiency in an infant with fatal bacille Calmette–Guerin infection," *New Eng. J. Med.* 335:1956–1961 (1996).

Jouanguy et al., "Partial interferon–gamma receptor 1 deficiency in a child with tuberculoid," *Journal of Clinical Investigations* 100:2658–2664 (1997).

Kallinowski et al., "Prevalence of enteropathogenic bacteria in surgically treated chronic inflammatory bowel disease," *Hepato–Gastroenterol.* 45:1552–1558 (1998).

Kullberg et al., "*Helicobacter hepaticus* triggers colitis in specific–pathogen–free interleukin–10 (IL–10)–deficient mice through an IL–12– and gamma interferon–dependent mechanism," *Infect. Immun.* 66:5157–5166 (1998).

Levin et al., "Familial disseminated atypical mycobacterial infection in childhood: a human mycobacterial susceptibility gene?" *Lancet* 345:79–83 (1995).

Lichtman et al., "A rat model of ileal pouch–rectal anastomosis," *Inflamm. Bowel Dis.* 4:187–195 (1998).

Ma et al., "A genome–wide search identifies potential new susceptibility loci for Crohn's disease," *Inflam. Bowel Dis.* 5:271–278 (1999).

Mutchnick et al., "Defective in vitro gamma interferon production and elevated serum immunoreactive thymosin beta 4 levels in patients with inflammatory bowel disease," *Clin. Immunol. Immunopathol.* 47:84–92 (1988).

Nakashima et al., "The combination of polymorphisms within interferon–γ receptor 1 and receptor 2 associated with the risk of systemic lupus erythematosus," *FEBS LETT* 453:187–190 (1999).

Newport et al., "A mutation in the interferon–γ–receptor gene and susceptibility to mycobacterial infection," *New Eng. J. Med.* 335:1941–1949 (1996).

Nicholls et al., "Pouchitis: Risk factors, etiology, and treatment," *World J. Surg.* 22:347–351 (1998).

Noguchi et al., "Enhanced interferon–gamma production and B7–2 expression in isolated intestinal mononuclear cells from patients with Crohn's disease," *J. Gastroenterol.* 30(S8):52–55 (1995).

Nguyen et al., "Severe gastrointestinal hemorrhage due to Mycobacterium Avium complex in a patient receiving immunosuppressive therapy," *Am. J. Gastroenterol.* 94:232–235 (1999).

Penna et al., "Pouchitis After Ileal Pouch Anal Anastomosis for Chronic Ulcerative Colitis Occurs With Increased Frequency in Patients with Associated Primary Sclerosing Cholangitis," *Gastroenterol.* 106:A751 (1994).

Rubinstein and Fisher, "Pouchitis: pathogenesis, diagnosis, and management," *Gastroenterologist* 4:129–133 (1996).

Rugtveit et al., "Cytokine profiles differ in newly recruited and resident subsets of mucosal macrophages from inflammatory bowel disease," *Gastroenterology* 112:1493–1505 (1997).

Sandborn et al., "Antineutrophil cytoplasmic antibody correlates with chronic pouchitis after ileal pouch–anal anastomosis," *Am. J. Gastroenterol.* 90:740–747 (1995).

Sandborn, "Pouchitis following ileal pouch–anal anastomosis: Definition, pathogenesis, and treatment," *Gastroenterol.* 107:1856–1860 (1994).

Stallmach et al., "IgG, albumin, and sCD44 in whole–gut lavage fluid are useful clinical markers for assessing the presence and activity of pouchitis," *Int. J. Colorectal Dis.* 14:35–40 (1999).

Stallmach et al., "Increased state of activation of CD4 positive T cell and elevated interferon γ production in pouchitis," *Gut* 43:499–505 (1998).

Stokkers et al., "Inflammatory bowel disease and the genes for the natural resistance–associated macrophage protein–1 and the interferon–γ receptor 1," *Int. J. Colorect. Dis.* 14:13–17 (1999).

Tanaka et al., "Association of the interferon–γ receptor variant (Val14Met) with systemic lupus erythematosus," *Immunogenetics* 49:266–271 (1999).

Watanabe et al., "Tumor necrosis factor and interferon–γ augment anticolon antibody–dependent cellular cytotoxicity in ulcerative colitis," *Immunopharm. Immunotoxicol.* 18:15–26 (1996).

\* cited by examiner

FIG. 1

1    ctacatagac atgatcatat tgtatagtat atatgattg tgtattgctt taagcatata 61   ttgtactcat gctttgatga ttatccttgt gtgtgtgtgt gtgtgtgtgt
         Primer A                              Microsatellite repeat 121  gtgtgtgtgt gtatacatat atttttttcc ttaggatttt tttagaatag atttcatagg 181  tttaaaattt tatgatgcaa gtatattttc gaggaatgga aatataggct gaagagccag 241  aacaaacact aaaaattcaat actaataact tcaagccatt atatgaag
                  Primer B

SEQUENCE LISTING

```
<160> NUMBER OF SEQ ID NOS:  3

<210> SEQ ID NO 1
<211> LENGTH: 288
<212> TYPE: DNA
<213> ORGANISM: Homo sapien

<400> SEQUENCE: 1
ctacatagac atgatcatat tgtatagtat atatgatttg tgtattgctt taagcatata        60
ttgtactcat gctttgatga ttatctttgt gtgtgtgtgt gtgtgtgtgt gtgtgtgtgt       120
gtgtgtgtgt gtatacatat attttttttcc ttaggatttt tttagaatag atttcatagg      180
tttaaaattt tatgatgcaa gtatattttc gaggaatgga aatataggct gaagagccag       240
aacaaacact aaaattcaat actaataact tcaagccatt atatgaag                    288

<210> SEQ ID NO 2
<211> LENGTH: 24
<212> TYPE: DNA
<213> ORGANISM: Homo sapien

<400> SEQUENCE: 2
tgaattttag tgtttgttct ggct                                                24

<210> SEQ ID NO 3
<211> LENGTH: 24
<212> TYPE: DNA
<213> ORGANISM: Homo sapien

<400> SEQUENCE: 3
catgctttga tgattatctt tgtg                                                24
```

GENETIC TESTING FOR DETERMINING THE RISK OF POUCHITIS DEVELOPMENT

This invention was made with government support under NIDDK Grant DK46763. The Government may have certain rights in this invention.

BACKGROUND OF THE INVENTION

1. Field of the Invention

The invention relates generally to the fields of autoimmunity and inflammatory bowel disease and more specifically to the development of pouchitis in patients with ulcerative colitis.

2. Background Information

Inflammatory bowel disease (IBD) is the collective term used to describe two gastrointestinal disorders of unknown etiology: Crohn's disease (CD) and ulcerative colitis (UC). The course and prognosis of IBD, which occurs world-wide and is reported to afflict as many as two million people, varies widely. Onset of IBD is predominantly in young adulthood with diarrhea, abdominal pain, and fever the three most common presenting symptoms. The diarrhea may range from mild to severe and in ulcerative colitis often is accompanied by bleeding. Anemia and weight loss are additional common signs of IBD. Ten percent to fifteen percent of all patients with IBD will require surgery over a ten year period. In addition, patients with IBD are at increased risk for the development of intestinal cancer. Reports of an increasing occurrence of psychological problems, including anxiety and depression, are perhaps not surprising symptoms of what is often a debilitating disease that strikes people in the prime of life.

Progress has been made in diagnosing IBD and in distinguishing, in many cases, Crohn's disease from ulcerative colitis. However, Crohn's disease and ulcerative colitis each can represent a collection of heterogeneous disease types that affect the gastrointestinal tract and produce similar symptoms. One aspect of the heterogeneity associated with inflammatory bowel disease is revealed by the stark contrast in outcomes seen following colectomy for treatment of uncontrolled ulcerative colitis. The preferred procedure is abdominal colectomy with ileal pouch anal anastomosis (IPAA), whereby the diseased colonic mucosa is removed while continence is maintained through creation of an ileal reservoir or "pouch." Although a subgroup of ulcerative colitis patients experience a favorable outcome following surgery, in the ten years after surgery almost 50% develop "pouchitis," an inflammation of the pouch that can mimic the original symptoms of ulcerative colitis. In some patients, the recurrent symptoms of pouchitis are as debilitating as the symptoms present prior to surgery. Thus, for those who suffer from recurrent or "chronic" pouchitis, surgical treatment of ulcerative colitis provides little or no therapeutic value.

A genetic method of determining the subgroup of ulcerative colitis patients at increased risk for development of pouchitis or chronic pouchitis would be useful in the medical management of these patients following surgery and in identifying good candidates for surgical treatment. Unfortunately, a genetic method for predicting the development of pouchitis or chronic pouchitis currently is not available. Thus, there is a need for a convenient and non-invasive genetic method of determining the risk of developing pouchitis or chronic pouchitis following pouch surgery. The present invention satisfies this need and provides related advantages as well.

SUMMARY OF THE INVENTION

The present invention provides a method of determining a risk of pouchitis development following a surgical procedure where an internal pouch is created in a patient with ulcerative colitis. The method is practiced by determining in the patient the presence or absence of a pouchitis-associated allele linked to an interferon γ receptor locus, where the presence of the pouchitis-associated allele indicates an increased risk of pouchitis development. The interferon γ receptor locus to which the pouchitis-associated allele is linked can be, for example, an interferon γ receptor 1 gene. A pouchitis-associated allele useful in the invention can be, for example, an allele located within the sixth intron of the interferon γ receptor 1 gene, such as the FA1 microsatellite 171 allele. In one embodiment, the pouchitis-associated allele is associated with chronic pouchitis with an odds ratio of at least 4 and a lower 95% confidence limit greater than 1. The methods of the invention can be useful in identifying good candidates for surgical treatment of ulcerative colitis and in the selective medical management of high risk patients following surgery, as described further below.

In a preferred embodiment, the invention provides a method of determining a risk of chronic pouchitis development following ileal pouch anal anastomosis in a patient with ulcerative colitis. In this method, one determines the presence or absence of an interferon γ receptor 1 FA1 microsatellite 171 allele in the patient, and the presence of the 171 allele indicates an increased risk of chronic pouchitis development.

In another embodiment, a method of the invention for determining a risk of pouchitis development in a patient with ulcerative colitis is practiced by obtaining from the patient material which contains nucleic acid including the FA1 microsatellite locus of the interferon γ receptor 1 gene; and enzymatically amplifying the nucleic acid to produce an amplified fragment containing the FA1 microsatellite locus, where the presence of the FA1 microsatellite 171 allele indicates an increased risk of pouchitis development. If desired, one can further include a step of electrophoresing the amplified fragment to determine whether a FA1 microsatellite 171 allele is present.

DETAILED DESCRIPTION OF THE INVENTION

Where medical management fails, ulcerative colitis can be cured by colectomy, although this is a radical treatment even with newly developed procedures to maintain continence. The preferred surgical procedure involves removal of a portion or the entire colon and the creation of an internal "pouch." Unfortunately, in some post-operative patients, symptoms similar to pre-operative ulcerative colitis arise in a condition termed "pouchitis." The methods of the invention are directed to the discovery of a convenient, non-invasive avenue for determining the risk of pouchitis development in an ulcerative colitis patient following surgery whereby an internal pouch is created.

Figure 1:
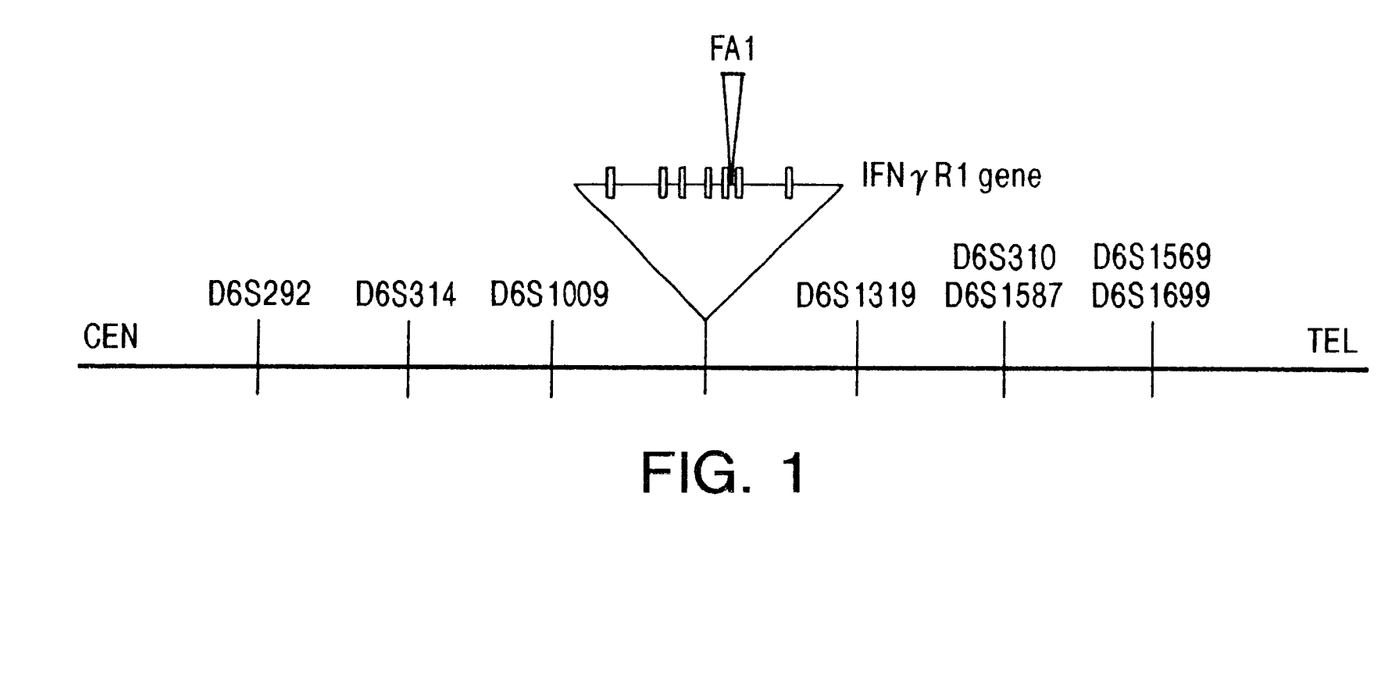
FIG. 1 shows the map of the interferon γ receptor 1 gene and the location of the interferon γ receptor 1 gene on chromosome 6 relative to other markers.

As disclosed herein, a genetic marker has been identified that is associated with an increased risk of pouchitis development in an ulcerative colitis patient following a surgical procedure such as ileal pouch anal anastomosis. In particular, an association was found between the likely development of pouchitis and the presence of a particular microsatellite allele, termed the FA1 "171 allele." The FA1 microsatellite, a repetitive DNA sequence containing a variable number of "CA" dinucleotides, is located in the sixth intron of the interferon γ receptor 1 gene (Altare et al., *Am. J. Hum Genet.* 62:723–726 (1998); see, also, FIGS. 1 and 2).

As disclosed in Example I, the FA1 microsatellite was characterized in 72 ulcerative colitis patients undergoing pouch surgery. Enzymatic amplification of a small fragment of genomic DNA containing the FA1 microsatellite was followed by electrophoresis to determine the size of the amplified fragment. As shown in Example I, of the patients who developed chronic pouchitis, 73.3% were positive for the 171 allele; in contrast, of patients who did not develop chronic pouchitis, only 39.3% were positive for the 171 allele (Table I). Statistical analysis confirmed that patients positive for the 171 allele have a significantly higher risk of developing chronic pouchitis following surgery as compared to patients lacking the 171 allele (p=0.02, odds ratio=4.4). Thus, the 171 allele is strongly associated with the development of chronic pouchitis following surgery and can be used to determine the risk of pouchitis development.

The methods of the invention are useful in the post-operative medical management of patients that have had pouchitis surgery. A patient determined to have an increased risk of pouchitis development according to a method of the invention can be treated prophylactically with any one of a number of therapies. Medical treatment for pouchitis includes antibiotics such as metronidazole, ciprofloxacin, amoxicillin or clavulanic acid, erythromycin and tetracycline; anti-inflammatory drugs such as mesalamine enemas, sulfasalazine and oral mesalamine; immunosuppressive drugs such as steroid enemas, oral steroids, azathioprine and cyclosporine enemas; nutritional agents such as short-chain fatty acid enemas or suppositories and glutamine suppositories; and inhibitors of oxygen radicals such as allopurinol (see, for example, Sandborn, *Gastroenterol.* 107:1856–1860 (1994); Hanauer, *New Engl. J. Med.* 334(13):841–848 (1996)).

The methods of the invention are particularly useful for allowing the selective treatment of patients at increased risk for developing pouchitis and permitting low-risk patients to avoid the side-effects of unnecessary therapy. For example, side-effects associated with antibiotic treatment, which is a preferred course of therapy for pouchitis, make it undesirable to place low-risk patients on these drugs unnecessarily. The methods of the invention, which allow treatment of a patient with an increased risk of developing pouchitis before clinical symptoms are detectable, also can prevent development of the chronic form of pouchitis through early intervention. Accordingly, the methods of the invention for determining the risk of developing pouchitis can be useful in the earlier and more selective treatment of ulcerative colitis patients that have had pouch surgery.

Thus, the present invention provides a method of determining a risk of pouchitis development following a surgical procedure whereby an internal pouch is created in a patient with ulcerative colitis. The method is practiced by determining the presence or absence in the patient of a pouchitis-associated allele linked to an interferon γ receptor locus, where the presence of the pouchitis-associated allele indicates an increased risk of pouchitis development. In a method of the invention, the interferon γ receptor locus can be, for example, an interferon γ receptor 1 gene (IFNGR1), and the pouchitis-associated allele can be within IFNGR1, for example, in the sixth intron of IFNGR1. In a preferred embodiment, the pouchitis-associated allele is an IFNGR1 FA1 microsatellite allele, such as the 171 allele. A method of the invention can be particularly useful for determining a risk of chronic pouchitis development following ileal pouch anal anastomosis.

Ulcerative colitis is a disease of the large intestine characterized by chronic diarrhea with cramping, abdominal pain, rectal bleeding, and loose discharges of blood, pus and mucus. The manifestations of ulcerative colitis vary widely. A pattern of exacerbations and remissions typifies the clinical course of most ulcerative colitis patients (70%), although continuous symptoms without remission are present in some patients with ulcerative colitis. Local and systemic complications of ulcerative colitis include arthritis, eye inflammation such as uveitis, skin ulcers and liver disease. In addition, ulcerative colitis and especially long-standing, extensive disease is associated with an increased risk of colon carcinoma.

Several pathologic features characterize ulcerative colitis in distinction to other inflammatory bowel diseases. Ulcerative colitis is a diffuse disease that usually extends from the most distal part of the rectum for a variable distance proximally. The term left-sided colitis describes an inflammation that involves the distal portion of the colon, extending as far as the splenic flexure. Sparing of the rectum or involvement of the right side (proximal portion) of the colon alone is unusual in ulcerative colitis. The inflammatory process of ulcerative colitis is limited to the colon and does not involve, for example, the small intestine, stomach or esophagus. In addition, ulcerative colitis is distinguished by a superficial inflammation of the mucosa that generally spares the deeper layers of the bowel wall. Crypt abscesses, in which degenerated intestinal crypts are filled with neutrophils, also are typical of ulcerative colitis (Rubin and Farber, *Pathology* (Second Edition) Philadelphia: J.B. Lippincott Company (1994)).

As used herein, the term "ulcerative colitis" is synonymous with "UC" and means a disease having clinical features of left-sided colonic disease accompanied by a characteristic endoscopic or histopathologic feature of ulcerative colitis. Clinical features of left-sided colonic disease, as used herein, are rectal bleeding, urgency and tenesmus. The rectal bleeding may be accompanied by mucus discharge. Clinical treatment of ulcerative colitis can include treatment with topical therapy and recommended or performed total or near-total colectomy.

A characteristic endoscopic feature of ulcerative colitis, which when present with clinical features of left-sided colonic disease indicates ulcerative colitis, is inflammation that is more severe distally than proximally or continuous inflammation. Additional typical endoscopic features that may be present in ulcerative colitis include inflammation extending proximally from the rectum or the presence of shallow ulcerations or the lack of deep ulcerations.

A characteristic histopathologic feature of ulcerative colitis, which when present with clinical features of left-sided colonic disease indicates ulcerative colitis, is homogeneous, continuous, predominantly superficial inflammation or a lack of "focality" within biopsy specimens. Additional typical histopathologic features that may be present in ulcerative colitis include the presence of crypt abscesses or a lack of granulomas.

As used herein, the term "patient with ulcerative colitis" means a patient having ulcerative colitis, as defined by the presence of clinical features of left-sided colonic disease accompanied by a characteristic endoscopic or histopathologic feature of ulcerative colitis as defined herein.

In the event that ulcerative colitis is unresponsive to medical therapy, surgical removal of the colon and creation of an internal pouch is an option that can remedy the painful symptoms of the disease. An unfortunate complication of pouch surgery can be the development of pouchitis. Pouchitis will often present as diarrhea accompanied by additional variable symptoms including abdominal cramping, fecal urgency and bleeding, or fever and can be diagnosed clinically by an increase of at least three stools per day above the post-operative base-line (Sandborn et al., *Am. J. Gastroenterol.* 90:740–747 (1995)). Characteristic endoscopic features of pouchitis are granularity, friability, loss of vascular pattern, mucous exudate or ulceration of the pouch. As used herein, the term "pouchitis" means a non-specific inflammation of a surgically created reservoir that is manifest clinically by diarrhea combined with one or more of the characteristic endoscopic features of pouchitis. The term pouchitis encompasses early-onset, acute and chronic pouchitis and includes treatment-responsive and treatment-resistant forms of chronic pouchitis, discussed below.

Pouchitis can develop months or years following pouch surgery. The cumulative frequency of pouchitis increases with time such that 15%, 36% or 46% of patients develop pouchitis 1, 5 or 10 years, respectively, after pouch surgery (Penna et al., *Gastroenterol.* 106:A751 (1994)). Early-onset pouchitis refers to a form of pouchitis that develops within twelve months of a surgical procedure whereby colon is removed and an internal pouch is created.

Pouchitis can occur acutely or as a chronic condition. Acute pouchitis can occur as a single event or as intermittent relapses with pouchitis-free intervals during which suppressive therapy is not required. In contrast, chronic pouchitis, which accounts for about five percent of cases following IPAA, is characterized by persistent symptoms of pouchitis despite adequate medical therapy, or by the need for continuous medical suppressive therapy with a prompt recurrence of symptoms if medical therapy is discontinued. Chronic pouchitis can be treatment-responsive, requiring ongoing suppressive therapy, or can be treatment-resistant.

As used herein, the term "chronic pouchitis" means intermittent or continuous recurrent pouchitis that requires continuous medical suppressive therapy or pouchitis that is characterized by persistent symptoms despite medical treatment.

As used herein, the term "patient" means an animal, such as a human or non-human mammal, capable of developing pouchitis.

As used herein, the term "surgical procedure whereby an internal pouch is created" is synonymous with "pouch surgery" and means a surgical procedure that results in creation of an internal reservoir for maintenance of continence, often involving total or near-total colectomy. The internal reservoir created can be, for example, an ileal reservoir or ileoanal reservoir. A common surgical procedure whereby an internal pouch is created is ileal pouch anal anastomosis.

The methods of the invention are useful for determining a risk of pouchitis development in an ulcerative colitis patient undergoing surgery such as ileal pouch anal anastomosis. The term "increased risk," as used herein in reference to pouchitis development indicated by the presence of a pouchitis-associated allele, means a probability of pouchitis development that is significantly higher than the probability of pouchitis development for a patient lacking a pouchitis-associated allele.

The methods of the invention rely on a pouchitis-associated allele that is linked to an interferon γ receptor locus. As used herein, the term "linked" means that two genetic loci have a tendency to be inherited together as a result of their proximity. If two genetic loci are linked and are polymorphic, a specific allele at one locus can serve as a marker for the inheritance of a specific allele at the second locus.

As used herein, the term "interferon γ receptor locus" means a locus encoding a subunit of an interferon γ receptor. A interferon γ receptor locus can be, for example, the human interferon γ receptor 1 locus (IFNGR1) or the interferon γ receptor 2 locus (IFNGR2). The sequence for human IFNGR1 is available, for example, as GenBank Accession number AL050337, and the sequence for the corresponding transcribed mRNA of interferon γ receptor 1 can be found, for example, as GenBank Accession number J03143. The sequence for the transcribed mRNA of human interferon γ receptor 2 is available, for example, as GenBank Accession number NM_005534.

The methods of the invention rely on a pouchitis-associated allele. As used herein, the term "pouchitis-associated allele" means a stably heritable molecular variation that tends to be inherited together with an increased risk of pouchitis development more often than would be expected according to traditional Mendelian genetics. A pouchitis-associated allele can be, for example, an allele linked to the FA1 microsatellite 171 allele, or can be the FA1 microsatellite 171 allele itself (see Example I).

A pouchitis-associated allele useful in a method of the invention can be, for example, a microsatellite (ms), single nucleotide polymorphism (snp) or a variable number tandem repeat (VNTR) polymorphism that tends to be inherited together with increased risk of pouchitis development. A microsatellite can be two or more repeats of two nucleotides, three nucleotides, four nucleotides or five nucleotides; dinucleotide repeats often seen in microsatellites include CA, TA, GA, AC, AG or GC repeats, or the complement thereof. A microsatellite can contain, for example, 6 or more nucleotide repeats, 8 or more nucleotide repeats, 10 or more nucleotide repeats, 12 or more nucleotide repeats, 14 or more nucleotide repeats, 16 or more nucleotide repeats, 20 or more nucleotide repeats, 22 or more nucleotide repeats, or 24 or more nucleotide repeats. In addition to a variation of one or more nucleotides, such as a substitution, insertion or deletion of one or more nucleotides, one skilled in the art understands that a pouchitis-associated allele also can be a molecular variation such as abnormal methylation or other modification that does not produce a difference in the primary nucleotide sequence.

A pouchitis-associated allele can occur in an intron or exon or in sequences 5' or 3' to a coding sequence and may or may not affect gene product expression or activity. A pouchitis-associated allele within an interferon γ receptor gene can result, for example, in production of a less active or inactive interferon γ receptor gene product or a reduced amount of a interferon γ receptor gene product. A pouchitis-associated allele within an interferon γ receptor gene also can be located in an intron or in a 5' or 3' regulatory sequence and can influence the regulation of transcription or translation or splicing of an interferon γ receptor-encoding mRNA. Such an allele can, therefore, result in a change in interferon γ receptor gene expression level or expression of an interferon γ receptor gene product variant. Where a pouchitis-associated allele is a nucleotide modification resulting in one or more amino acid substitutions, deletions or insertions in an interferon γ receptor coding sequence to produce an interferon γ receptor gene product variant, the variant can be a polypeptide that lacks the ability to transduce a signal after binding interferon γ, or can be a soluble interferon γ receptor polypeptide that functions as a dominant negative molecule.

In a preferred embodiment, the risk of pouchitis development is determined using the FA1 microsatellite 171 allele. A pouchitis-associated allele such as the FA1 microsatellite 171 allele is defined in comparison to a Centre d'Etude du Polymorphisme Humain (CEPH) reference individual such as the individual designated 1347-02 (Dib et al., *Nature* 380:152–154 (1996), using commercially available reference DNA obtained, for example, from PE Biosystems (Foster City, Calif.). As used herein, the "term FA1 microsatellite 171 allele" is synonymous with "171 allele" and means an allele of the interferon γ FA1 microsatellite which has a size of 171 basepairs (bp) when amplified with primers SEQ ID NOS:2 and 3 in an assay in which the heterozygous FA1 alleles of CEPH reference individual 1347-02 have sizes of 189 and 191 basepairs. The FA1 microsatellite is polymorphic and has a varing number of repeats in different individuals. For example, the interferon γ receptor 1 FA1 microsatellite contains a 21 "CA" repeat at residues 64213–64254 of GenBank Accession number AL050337. Another example of the FA1 microsatellite is available as GenBank Accession number U84721, where it contains 22 "GT" repeats (the complement of the CA repeat) at residues 89–132 of U84721.

As disclosed herein in Example I, the presence of a 171 allele can be conveniently detected, for example, by gel electrophoresis of a 171 basepair fragment generated by amplification with primers 5'-TET-TGA ATT TTA GTG TTT GTT CTG GCT-3' (SEQ ID NO:2) and 5'-CAT GCT TTG ATG ATT ATC TTT GTG-3' (SEQ ID NO:3). One skilled in the art understands that a single copy of the 171 allele is sufficient to indicate a high risk of pouchitis development; thus, an ulcerative colitis patient heterozygous for the 171 allele has a probability of developing pouchitis that is significantly higher than the probability of an ulcerative colitis patient who does not have any copies of the 171 allele.

It is understood that the designation "171" reflects the size of a fragment obtained by amplification of the FA1 microsatellite locus with a particular primer pair (SEQ ID NOS:2 and 3). In view of the size of the 171 allele relative to the 189 and 191 alleles of CEPH reference individual 1347-02 and the gene sequence in the region of the FA1 microsatellite, one skilled in the art readily can design a variety of alternative primer pairs that can be useful in the methods of the invention. With alternative primer pairs, the 171 allele will have a different characteristic size, which will be 18 and 20 basepairs smaller than the size of the heterozygous alleles of CEPH reference individual 1347-02 when amplified with the same alternative primer pair.

In one embodiment, the invention provides a method of determining a risk of pouchitis development in a patient with ulcerative colitis by determining the presence or absence of a pouchitis-associated allele linked to an interferon γ locus using enzymatic amplification of nucleic acid from the patient. In other embodiments, the presence or absence of a pouchitis-associated allele is determined by electrophoretic analysis, restriction fragment length polymorphism analysis, sequence analysis, or a combination of these techniques.

The invention also provides a method of determining a risk of pouchitis development in a patient with ulcerative colitis by obtaining from the patient material which contains nucleic acid including the FA1 microsatellite locus, and enzymatically amplifying the nucleic acid to produce an amplified fragment containing the FA1 microsatellite locus, or a portion thereof. One skilled in the art understands that the amplified fragment need only include part of the recited locus. Thus, for example, an amplified fragment need only contain that portion of the FA1 microsatellite locus containing the variable-length CA repeat and need not contain, for example, the sequence of GenBank Accession No. U84721 in its entirety.

In another embodiment, the invention provides a method of determining a risk of pouchitis development in a patient with ulcerative colitis by obtaining from the patient material which contains nucleic acid including the FA1 microsatellite locus, enzymatically amplifying the nucleic acid to produce an amplified fragment containing the FA1 microsatellite locus, and electrophoresing the amplified fragment, thereby determining whether a FA1 microsatellite 171 allele is present. The presence of the 171 allele indicates an increased risk of pouchitis development.

As used herein, the term "material" means any biological matter from which nucleic acid can be prepared. The term material encompasses whole blood, plasma, lymph, urine, breast milk, saliva, skin, hair follicle, cervix, cheek, or other bodily fluid or tissue that contains nucleic acid. Preferred materials are cheek or whole blood, which can be obtained readily by non-invasive means and used to prepare genomic DNA for enzymatic amplification.

As used herein, the term "nucleic acid" means a polynucleotide such as deoxyribonucleic acid (DNA) or ribonucleic acid (RNA) and encompasses both single-stranded and double-stranded nucleic acid. Total genomic DNA is a particularly useful nucleic acid with which to practice a method of the invention.

The presence or absence of a pouchitis-associated allele can be determined using one of a variety of molecular genotyping methods well known in the art. Such genotyping methods include, for example, electrophoresis-based methods, sequencing analyses, restriction fragment length polymorphism analyses, allele-specific oligonucleotide hybridization, heteroduplex mobility assays, single strand conformational polymorphism analyses, denaturing gradient gel electrophoresis, cleavase fragment length polymorphism analyses and rolling circle amplification. One skilled in the art understands that electrophoresis based methods including denaturing gradient gel electrophoresis and heteroduplex mobility assays are particularly useful for determining the presence or absence of a pouchitis-associated allele that is a microsatellite allele. See, in general, Birren et al. (Eds.) *Genome Analysis: A Laboratory Manual* Volume 1 (Analyzing DNA) New York, Cold Spring Harbor Laboratory Press (1997) and Ausubel et al., *Current Protocols in Molecular Biology* Chapter 2 (Supplement 49) John Wiley & Sons, Inc. New York (2000)).

In one embodiment, the presence of a pouchitis-associated allele is determined using electrophoretic analysis. Electrophoresis, including gel or capillary electrophoresis, can be useful in separating amplified fragments containing alleles that differ in size. The term "electrophoretic analysis" or "electrophoresing," as used herein in reference to one or more nucleic acids such as amplified fragments, means a process whereby charged molecules are moved through a stationary medium under the influence of an electric field. Electrophoretic migration separates nucleic acids primarily on the basis of their charge, which is in proportion to their size, with smaller nucleic acids migrating more quickly. The term electrophoretic analysis or electrophoresing includes analysis using both slab gel electrophoresis, such as agarose or polyacrylamide gel electrophoresis, and capillary electrophoresis. Capillary electrophoretic analysis, which generally occurs inside a small-diameter (50–100-$\mu$m) quartz capillary in the presence of high (kilovolt-level) separating voltages with separation times of a few minutes, can be particularly useful in a method of the invention. Using capillary electrophoretic analysis, nucleic acids such as amplified fragments are conveniently detected by UV absorption or fluorescent labeling, and single-base resolution can be obtained on fragments up to several hundred base pairs. Such methods of electrophoretic analysis, and variants thereof, are well known in the art as described, for example, in Ausubel et al., supra, 2000.

Restriction fragment length polymorphism (RFLP) analysis also can be useful for determining the presence or absence of a pouchitis-associated allele in a method of the invention (Jarcho et al. in Dracopoli et al., *Current Protocols in Human Genetics* pages 2.7.1–2.7.5, John Wiley & Sons, New York Innis et al.,(Ed.), *PCR Protocols*, San Diego: Academic Press, Inc. (1990)). As used herein, the term "restriction fragment length polymorphism analysis" is synonymous with "RFLP analysis" and means any method for distinguishing genetic polymorphisms using a restriction enzyme, which is an endonuclease that catalyzes the degradation of nucleic acid and recognizes a specific base sequence, generally a palindrome or inverted repeat. One skilled in the art understands that the use of RFLP analysis can depend upon an enzyme that can differentiate two alleles at a polymorphic site, or, alternatively, RFLP analysis can depend on the sizes of fragments when cleaved at the same sites.

Sequence analysis also can be used to determine the presence or absence of a pouchitis-associated allele in a method of the invention. The term "sequence analysis," as used herein in reference to one or more nucleic acids such as amplified fragments, refers to any manual or automated process by which the order of nucleotides in a nucleic acid is determined. It is understood that the term sequence analysis encompasses chemical (Maxam-Gilbert) and dideoxy enzymatic (Sanger) sequencing as well as variations thereof. Thus, the term sequence analysis includes capillary array DNA sequencing, which relies on capillary electrophoresis and laser-induced fluorescence detection and can be performed using, for example, the MegaBACE 1000 or ABI 3700. Sequence analysis can also be carried out using gel electrophoresis and detection methods such as fluorescence detection, radionuclide detection, and the like. Gel electrophoresis can be performed using, for example, the ABI 377 DNA sequencer. Also encompassed by the term sequence analysis are thermal cycle sequencing (Sears et al., *Biotechniques* 13:626–633 (1992)); solid-phase sequencing (Zimmerman et al., *Methods Mol. Cell Biol.* 3:39–42 (1992) and sequencing with mass spectrometry such as matrix-assisted laser desorption/ionization time-of-flight mass spectrometry MALDI-TOF MS (Fu et al., *Nature Biotech*. 16: 381–384 (1998)). The term sequence analysis also includes, for example, sequencing by hybridization (SBH), which relies on an array of all possible short oligonucleotides to identify a segment of sequences present in an unknown DNA (Chee et al., *Science* 274:61–614 (1996); Drmanac et al., *Science* 260:1649–1652 (1993); and Drmanac et al., *Nature Biotech*. 16:54–58 (1998)). One skilled in the art understands that these and additional variations are encompassed by the term sequence analysis as defined herein. See, in general, Ausubel et al., supra, 2000; Chapter 7.

Cleavase fragment length polymorphism analysis also can be useful in the methods of the invention. Cleavase is an enzyme that cleaves junctions between single- and double-stranded regions of DNA. The gel filtration migration pattern of a DNA sample after cleavase digestion can be unique for each variant of the DNA sample according to the number of single- and double-stranded regions, the equilibrium between single- and double-stranded regions of the DNA, and the number of nucleotides in each cleavage fragment. This unique pattern, or "bar code" can be used to rapidly genotype a nucleic acid sample according to its migration pattern (see, for example, Tondella et al. *J. Clin. Microbiol.*, 37:2402–2407 (1999); and U.S. Pat. Nos. 5,719,028 and 5,846,717).

Denaturing gradient gel electrophoresis (DGGE) also can be used to determine the presence or absence of a pouchitis-associated allele in a method of the invention. In DGGE, double-stranded DNA is electrophoresed in a gel containing an increasing concentration of denaturant; double-stranded fragments made up of mismatched alleles have segments that melt more rapidly, causing such fragments to migrate differently as compared to perfectly complementary sequences (Sheffield et al., "Identifying DNA Polymorphisms by Denaturing Gradient Gel Electrophoresis" in Innis et al., supra, 1990).

A heteroduplex mobility assay (HMA) is another well known assay that can be used to determine the presence or absence of a pouchitis-associated allele. HMA is useful for detecting the presence of a polymorphic sequence since a DNA duplex carrying a mismatch has reduced mobility in a polyacrylamide gel compared to the mobility of a perfectly base-paired duplex (Delwart et al., *Science* 262:1257–1261 (1993); White et al., *Genomics* 12:301–306 (1992)).

The technique of single strand conformational polymorphism (SSCP) also can be used to determine the presence or absence of a pouchitis-associated allele in a method of the invention (see Hayashi, *PCR Methods Applic*. 1:34–38 (1991)). This technique can be used to detect mutations based on differences in the secondary structure of single-strand DNA that produce an altered electrophoretic mobility upon non-denaturing gel electrophoresis. Polymorphic fragments are detected by comparison of the electrophoretic pattern of the test fragment to corresponding standard fragments containing known alleles.

Allele-specific oligonucleotide hybridization also can be used to determine the presence or absence of a pouchitis-associated allele in a method of the invention. Allele-specific oligonucleotide hybridization is based on the use of a labeled oligonucleotide probe having a sequence perfectly complementary, for example, to the nucleotides of a pouchitis-associated allele. Under appropriate conditions, the allele-specific probe hybridizes to a nucleic acid containing the pouchitis-associated allele but does not hybridize to one or more other alleles, which have one or more nucleotide mismatches as compared to the probe. If desired, a second allele-specific oligonucleotide probe that matches an alternate allele also can be used. Similarly, the technique of allele-specific oligonucleotide amplification can be used to selectively amplify, for example, a pouchitis-associated allele by using an allele-specific oligonucleotide primer that is perfectly complementary to the nucleotide sequence of the pouchitis-associated allele but which has one or more mismatches as compared to other alleles (Mullis et al. (Eds.), *The Polymerase Chain Reaction*, Birkhäuser, Boston, (1994)). One skilled in the art understands that the one or more nucleotide mismatches that distinguish between the pouchitis-associated allele and one or more other alleles are preferably located in the center of an allele-specific oligonucleotide primer to be used in allele-specific oligonucleotide hybridization. In contrast, an allele-specific oligonucleotide primer to be used in PCR amplification preferably contains the one or more nucleotide mismatches that distinguish between the pouchitis-associated and other alleles at the 3' end of the primer.

Rolling circle amplification also can be used to determine the presence or absence of a pouchitis-associated allele in a method of the invention (Baner et al., *Nucleic Acids Res.* 26:5073–5078 (1998), and Lizardi et al., *Nat. Genet.* 19:225–232 (1998)). In rolling circle amplification, a linear probe is designed so that the 5' and 3' ends of the probe hybridize to immediately adjacent nucleotides in a specific nucleotide sequence. If the sample DNA has the specific sequence, the 5' and 3' ends are adjacent and the probe can be circularized using ligase. Sample DNA without the specific sequence will not result in the 5' and 3' ends hybridizing immediately adjacent one another, and therefore will not act as a successful template for circularization. The circularized probe can then be used in rolling circle replication to amplify the sequence prior to detection.

Other well-known approaches for determining the presence or absence of a pouchitis-associated allele include automated sequencing and RNAase mismatch techniques (Winter et al., *Proc. Natl. Acad. Sci.* 82:7575–7579 (1985)). Furthermore, one of skill in the art understands that amplification or cleavage methods described above also can be used in solid state methods, for example, using DNA microarrays for detection or as templates for enzymatic reactions (see Ausubel et al., supra, 2000). Similarly, mass spectroscopy can be used for the detection of cleavage or amplification products as described, for example, in U.S. Pat. Nos. 6,043,031, 5,605,798, and 5,547,835. It is understood that the methods of the invention can be practiced using these or other art-recognized assays for detecting polymorphic alleles.

In one embodiment, the strength of the association between a pouchitis-associated allele and an increased risk of pouchitis development is characterized by an odds ratio of at least 4 with a lower 95% confidence interval limit of at least 1. An odds ratio can be, for example, at least 3.0, 3.5, 4.0, 4.5, 5.0, 5.5 or 6.0 with a lower 95% confidence interval limit of at least 1, such as an odds ratio of at least 4 with a 95% confidence interval of 1.2 to 15.4 (see Table 1). As disclosed herein, 35% of ulcerative colitis patients positive for the 171 allele developed chronic pouchitis after IPAA, whereas only 11% of patients negative for the 171 allele developed chronic pouchitis. Kaplan-Meier survival analysis indicated that, in a group of 72 tested patients, the 171 allele was significantly associated with a higher risk of developing chronic pouchitis as compared to patients lacking the 171 allele. The odds ratio was 4.4 with a 95% confidence limit of at least 1.2. Methods for determining an odds ratio are well known in the art (see, for example, Schlesselman et al., *Case Control Studies: Design, Conduct and Analysis* Oxford University Press, New York (1982)).

As disclosed herein in Example I, the FA1 microsatellite 171 allele was associated with an increased risk of chronic pouchitis with a p value of 0.02. A "p value" or "probability value" is a term known in the art. In a test for association between an allele and a condition such as pouchitis, a p value measures the probability that the allele and the condition are associated by random or chance factors. A p value of 1.00 indicates that the probability is high, or certain, that the association of the allele and the condition is due to random or chance factors. This indicates that the allele does not influence the condition. A p value of 0.05 is a typical threshold in statistical testing of the association between an allele and a condition. A p value of 0.05 indicates that the "false positive rate," or rate that the test would falsely indicate that there is an association between the allele and the condition, is one of twenty tests. A pouchitis-associated allele can be associated with a high risk of developing pouchitis with, for example, a p value of equal to or less than 0.04, 0.03, 0.02, 0.01, 0.009, 0.008, 0.007, 0.006, 0.005, 0.004, 0.003, 0.002 or 0.001, or with a p value of equal to or less than 0.00095, 0.0009, 0.00085 or 0.0008. It is recognized that, in some cases, p values may need to be corrected, for example, to account for factors such as sample size (number of families), genetic heterogeneity (linked forms and unlinked forms), clinical heterogeneity, or canalytical approach (parametric or nonparametric method).

In another embodiment, the invention provides a method of determining a reduced risk of pouchitis development in a patient with ulcerative colitis following a surgical procedure whereby an internal pouch is created. The method consists of determining the presence or absence in said patient of a pouchitis-associated allele linked to an interferon γ receptor locus, where the absence of said pouchitis-associated allele indicates a reduced risk of pouchitis development.

The term reduced risk, as used herein in reference to pouchitis development indicated by the absence of a pouchitis-associated allele, refers to a probability of pouchitis development that is significantly lower than the probability of pouchitis development for a patient having a pouchitis-associated allele.

Previous work has demonstrated that the presence of a high pANCA titer (greater than 100 ELISA units/ml) can be used as an indicator of the risk of pouchitis development, and such methods are exemplified in U.S. Pat. No. 5,937,862, which is incorporated herein by reference. Furthermore, as disclosed herein, the presence of a pouchitis-associated 171 allele was found to correlate with an increased risk of pouchitis development, but did not correlate with the presence of a high pANCA titer (see Example IB). Therefore, a pouchitis-associated allele, such as the FA1 microsatellite 171 allele, and the presence of a high pANCA titer are independent indicators of a high risk of pouchitis development. These results indicate that genetic testing for the FA1 microsatellite 171 allele can be combined with serological testing for a high pANCA titer to produce a highly sensitive method of determining the risk of pouchitis development.

Thus, the present invention also provides a method that combines genetic and serological testing to determine a risk of pouchitis development following a surgical procedure whereby an internal pouch is created in a patient with ulcerative colitis. This method is practiced by determining the presence or absence in the patient of a pouchitis-associated allele linked to an interferon γ receptor locus; and determining the presence or absence of a high pANCA titer in the patient, where the presence of either the pouchitis-associated allele or a high pANCA titer indicates an increased risk of pouchitis development.

The results disclosed herein also relate to primary sclerosing cholangitis (PSC), a disease characterized by obliterative inflammatory fibrosis of the extrahepatic bile ducts with or without involvement of the intrahepatic ducts. The disease generally progresses in an unrelenting, albeit unpredictable, fashion to cirrhosis, portal hypertension, and death from liver failure. Primary sclerosing cholangitis can occur alone or in association with ulcerative colitis and less commonly with a variety of other diseases. Symptoms commonly include jaundice, puritis and nonspecific upper abdominal pain. Medical treatment of primary sclerosing cholangitis can include corticosteroids, antibiotics, immunosuppressants, and cholecystogues alone or in combination.

As disclosed in Example I, a significantly higher percentage of patients who developed primary sclerosing cholangitis were positive for the 171 allele (69.2%), as compared to patients without primary sclerosing cholangitis that were positive for the 171 allele (37.5%; p=0.019). These results indicate that the FA1 microsatellite 171 allele can be used as a diagnostic indicator of primary sclerosing cholangitis.

Thus, the present invention also provides a method of diagnosing primary sclerosing cholangitis by determining the presence or absence of an interferon γ receptor 1 FA1 microsatellite 171 allele in an individual, where the presence of the 171 allele is diagnostic of primary sclerosing cholangitis. This genetic method can be practiced using any of a variety of molecular techniques for determining the presence or absence of a polymorphic allele (see above).

Ulcerative colitis is recognized to be a heterogeneous disorder representing a number of distinct disease subtypes that affect the gastrointestinal tract and produce similar symptoms. The heterogeneity underlying ulcerative colitis can be reflected, for example, in variable responses to particular treatment strategies. An example of a disease subtype is the subgroup of ulcerative colitis patients with medically resistant ulcerative colitis (see U.S. Pat. No. 5,968,741, issued Oct. 19, 1999). These patients are unresponsive to steroids, 5-aminosalicylic acid (5-ASA), 6-mercaptopurine (6-MP), cyclosporine A, and the like. As a result of such resistance to standard treatments, this subgroup of ulcerative colitis patients typically requires more aggressive forms of medical treatment or colectomy.

Other examples of clinical subtypes include the pANCA-positive clinical subtype of Crohn's disease, which is characterized by features of ulcerative colitis in addition to the features that are typical of Crohn's disease. These pANCA-positive Crohn's disease patients suffer from a similar type of mucosal inflammation and respond similarly to a particular course of therapy and, furthermore, can benefit from some of the same therapeutic strategies that are efficacious in the medical management of ulcerative colitis, while other Crohn's disease patients are unresponsive (see U.S. Pat. No. 5,916,748, issued Jun. 29, 1999, and U.S. Pat. No. 5,874,233, issued Feb. 23, 1999).

In view of the above, one skilled in the art understands that the FA1 microsatellite allele also can be associated with a specific subtype of ulcerative colitis or Crohn's disease. A clinical subtype is a subgroup of patients having a particular disease, such as ulcerative colitis, whose features of disease are more similar to each other than to other patients with the same disease.

An exemplary subtype of ulcerative colitis is the subgroup of patients diagnosed as having ulcerative colitis that undergo pouch surgery and subsequently develop chronic pouchitis followed by extraintestinal complications, for example, inflammation similar to that seen in Crohn's disease. Such a population is described in Goldstein at al., *Am. J. Surg. Pathol.* 21:1343–1353 (1997). In accordance with the invention, the presence of a pouchitis-associated allele, such as the FA1 microsatellite 171 allele, can be used to identify this subtype of patients in which Crohn's-like complications develop following pouch surgery.

The invention also provides an isolated nucleotide probe that contains at least 15 nucleotides and selectively hybridizes under moderately stringent hybridization conditions with a nucleic acid molecule having nucleotides 63214–64213 of GenBank accession number AL050337 or a nucleic acid molecule having nucleotides 64255–65254 of GenBank accession number AL050337, provided that the nucleotide probe is not GenBank accession AL050337 or U84721. The invention also provides an isolated nucleotide probe that contains at least ten contiguous nucleotides of a nucleic acid molecule having nucleotides 63214–64213 of GenBank accession number AL050337 or a nucleic acid molecule having nucleotides 64255–65254 of GenBank accession number AL050337, provided that the nucleotide probe is not GenBank accession number AL050337 or U84721. An isolated nucleotide probe of the invention can have a length of, for example, at least 12, 15, 17, 18, 20, 21, 22, 23, 24 or 25 nucleotides. An isolated nucleotide probe of the invention can have a maximum length of, for example, at most 20, 25, 30, 35, 40, 60, 80, 100, 150 or 200 nucleotides.

Further provided by the invention is a kit for indicating the susceptibility of a patient to pouchitis development following a surgical procedure to treat ulcerative colitis. A kit of the invention contains two nucleotide probes that are capable of being used together in an amplification reaction to form an amplified fragment containing the FA1 microsatellite locus of the interferon γ receptor 1 gene, provided that neither of the two probes is GenBank accession number AL050337 or U84721.

The following examples are intended to illustrate but not limit the present invention.

EXAMPLE I

This example demonstrates that the interferon γ receptor 1 FA1 microsatellite 171 allele is associated with development of chronic pouchitis after ileal pouch anal anastomosis.

A. Association of the FA1 Microsatellite 171 Allele with Increased Risk of Chronic Pouchitis Blood samples were collected from 72 Caucasian patients with ulcerative colitis at the time of undergoing ileal pouch-anal anastomosis. Status of each patient with respect to pouchitis development was followed up on at least one occasion between 1 and 81 months following surgery (median follow up: 27 months following surgery). Follow up included assessment of clinically and endoscopically proven pouchitis by an investigator blinded to the genotype and pANCA status of the patient. Of the 72 patients evaluated, 36% (n=26) developed pouchitis, and 22% (n=16) were categorized as developing chronic pouchitis based on the criteria that the symptoms of pouchitis were recurrent.

Patients were genotyped for the FA1 microsatellite marker located in the sixth intron of the interferon γ receptor 1 gene, and analyzed for an association between an FA1 allele and the development of is chronic pouchitis. A specific FA1 allele, termed the 171 allele, was present in 34 of the 72 tested patients (47%). Of the patients that were positive for the 171 allele, 35% developed chronic pouchitis. In contrast, only 11% of the patients negative for the 171 allele developed chronic pouchitis. Furthermore, of the patients who developed chronic pouchitis, 73.3% were positive for the 171 allele; in contrast, of patients who did not develop chronic pouchitis, only 39.3% were positive for the 171 allele (Table I).

Kaplan Meier survival analysis confirmed that 171 allele-positive patients had a significantly higher risk of developing chronic pouchitis than 171 allele-negative patients (p=0.02, odds ratio=4.4, 95% confidence limit=1.2–15.4). These results indicate that the presence of the FA1 microsatellite 171 allele is an indicator of increased risk of chronic pouchitis developement in ulcerative colitis patients that have undergone ileal pouch anal anastomosis.

Similar analysis was carried out for 66 patients who were tested for extraintestinal complications, surgical indications, primary sclerosing colangitis and pouchitis. Of these 66 patients, 48 also were tested for pANCA levels. Similar to the findings with chronic pouchitis, patients who developed any form of pouchitis were more frequently positive for the 171 allele than those without pouchitis (p=0.039, see Table I). In addition, a significantly higher percentage of patients who developed primary sclerosing cholangitis (PSC) also were positive for the 171 allele (69.2%), relative to 37.5% of the patients without PSC that were positive for the 171 allele (p=0.019). Together, these results indicate that the FA1 171 allele can be used as a diagnostic indicator of the development of chronic pouchitis, pouchitis or primary sclerosing cholangitis.

Figure 2:
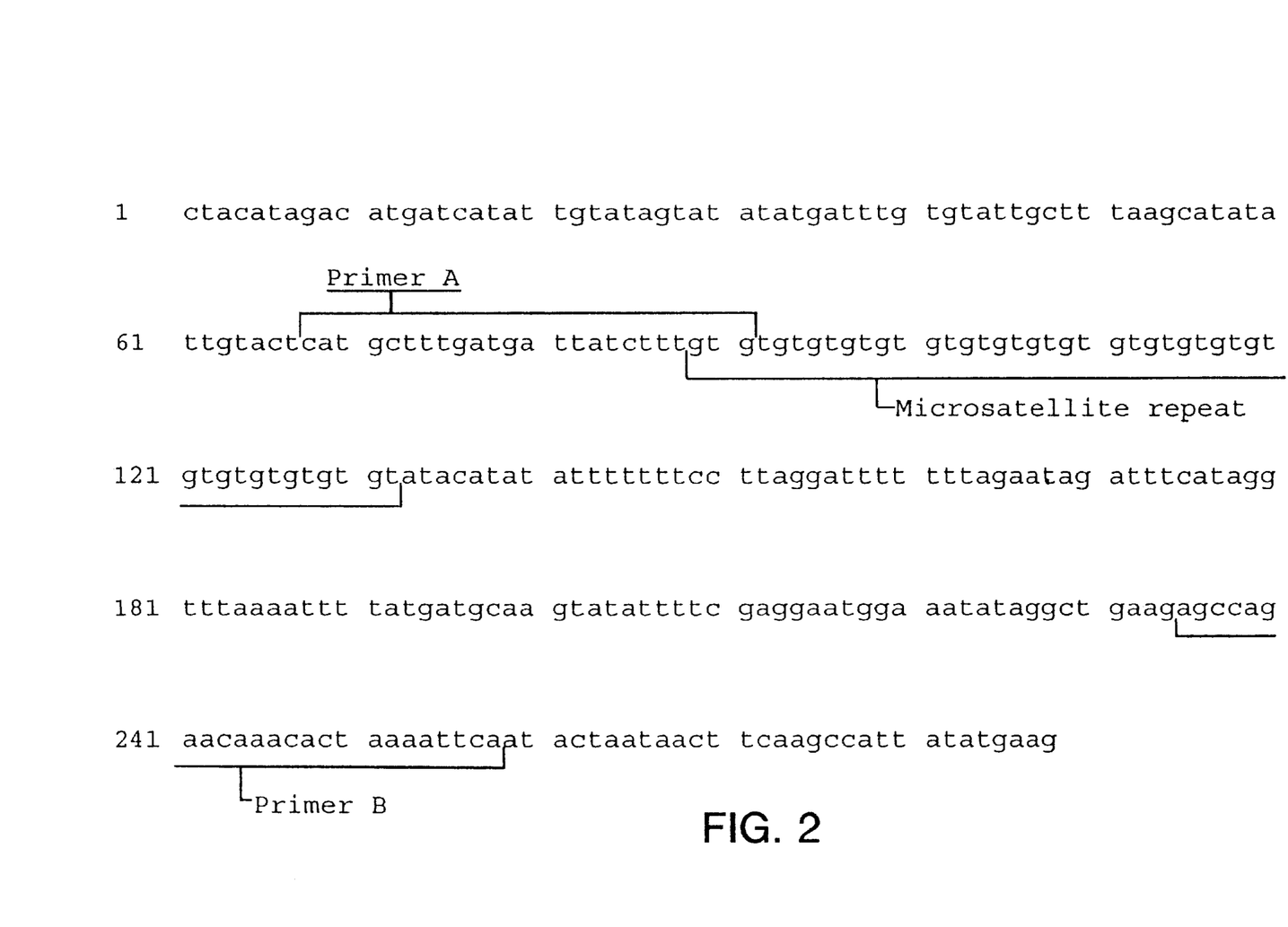
FIG. 2 shows the nucleotide sequence of the interferon γ receptor 1 FA1 microsatellite together with flanking nucleotides (Genbank accession U84721; SEQ ID NO:1). The microsatellite is marked in addition to primer A (SEQ ID NO:2) and primer B (SEQ ID NO:3).

Genotyping at the FA1 microsatellite locus was performed essentially as follows. Genomic DNA from each patient was amplified by the polymerase chain reaction (PCR) using primers based on the sequences flanking the FA1 microsatellite reported in GenBank accession number U84721 (FIG. 2). Primer A had the sequence 5'-TET-TGA ATT TTA GTG TTT GTT CTG GCT-3' (SEQ ID NO:2), and Primer B had the sequence 5'-CAT GCT TTG ATG ATT ATC TTT GTG-3' (SEQ ID NO:3) prepared by Research Genetics (Huntsville, Ala.). PCR amplification was carried out using Ampli-Taq Gold™ TaqI DNA polymerase according to the manufacturer's instructions (Perkin Elmer, Foster City, Calif.). Briefly, PCR was performed in a 20 µl volume containing 10 mM Tris-HCl buffer, pH 8.3; 50 mM KCl; 0.001% gelatin; 2.5 mM MgCl$_2$; 1 unit Ampli-Taq Gold™ TaqI DNA polymerase; 40–100 ng genomic DNA; and 200 µM each of dATP, dCTP, dTTP and dGTP. Thermal cycling was carried out as follows: 1 cycle of 95° C. for 10 minutes; 35 cycles of 95° C. for 30 seconds, 55° C. for 75 seconds, and 70° C. for 15 seconds; and 1 cycle of 70° C. for 10 minutes.

Figure 3:
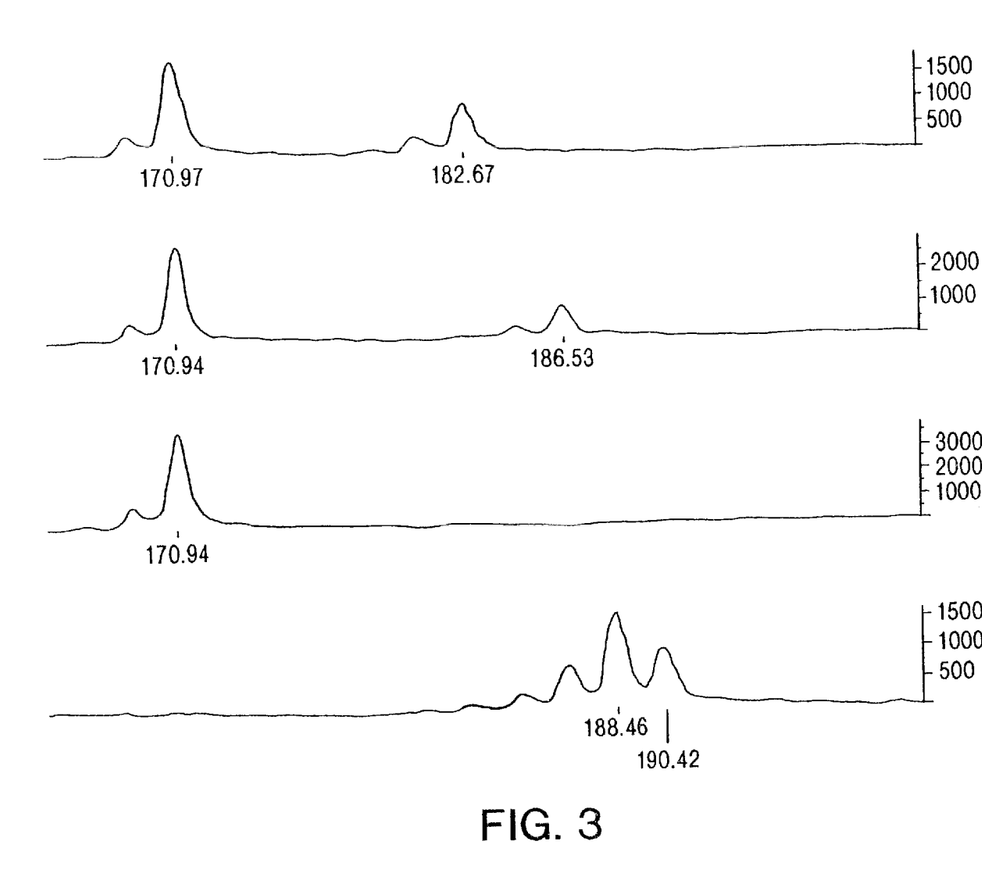
FIG. 3 shows chromatograms for individuals genotyped at the interferon γ receptor 1 FA1 microsatellite locus using primers SEQ ID NOS: 2 and 3. The top two chromatograms show patients heterozygous for the 171 allele; the third chromatogram shows a patient homozygous for the 171 allele; and the fourth chromatogram shows the heterozygous 189/191 alleles of CEPH reference individual 1347-02.

Amplified PCR products were analyzed as follows. PCR product samples were diluted from 1:5 to 1:20 with distilled deionized water. The diluted samples were loaded onto a 4.25% polyacrylamide/6 M urea gel, and electrophoresed for 2 to 2½ hours using an ABI Prism 377 DNA Sequencer (Perkin Elmer, Foster City, Calif.) according to a standard protocol provided by the manufacturer. The positions of the bands were assigned a size in accordance with size standards and methods suggested in the GenScan® Reference Guide (Perkin Elmer, Foster City, Calif., 1997). The heterozygous FA1 microsatellites from a reference individual, CEPH 1347-02, were used as internal standards; this individual has been shown to have the FA1 microsatellite 189 and 191 alleles. Under the conditions described above, the 189 and 191 alleles of CEPH 1347-02 had apparent sizes 188.5 and 190.4 bp, and the 171 allele had an apparent size of 170.9 (FIG. 3). Statistical methods were carried out using Statistical Analysis Software (Carey, N.J.). P values were calculated taking into account the ethnicity of the patients (Jewish versus non-Jewish), whether a patient was pANCA positive (at least 1 ELISA unit/ml), and whether a patient had high pANCA levels (at least 100 ELISA units/ml).

B. The FA1 Microsatellite 171 Allele and High pANCA Levels are Independently Associated with Development of Chronic Pouchitis Pre-operative high-levels of pANCA have been shown to be associated with chronic pouchitis after IPAA. pANCA status was determined in 52 of the patients in this study by Prometheus Laboratories, Inc. (San Diego, Calif.) according to the methods disclosed in U.S. Pat. No. 5,937,862, issued Aug. 17, 1999. Patients were categorized as having either high or low pANCA levels, where high pANCA levels were considered levels greater than or equal to 100 units/ml. Six of the 52 patients (12%) had high-level pANCA before colectomy and IPAA. Of these, five patients (83%) developed chronic pouchitis.

The relationship between pANCA levels and the FA1 171 allele was examined by stratified analysis. The results showed that the incidence of chronic pouchitis in 171 allele-positive patients was independent of pANCA status (p=0.010 for pANCA positive patients and p=0.011 for patients with high pANCA levels, see Table I). These results

TABLE I

| Trait | Percentage of patients with trait having 171 allele | Percentage of patients without trait having 171 allele | p value as a function of ethnicity | Odds Ratio (95% Confidence Limit) | p value as a function of pANCA level ≥100 | p value as a function of pANCA level >0 | p value as a function of ethinicity* |
|---|---|---|---|---|---|---|---|
| N = 66 patients (48 patients with pANCA information) | | | | | | | |
| Extra-intestinal complications | 55.6 | 49.1 | 0.779 | | | | 0.566 |
| Surgical indication | 53.9 | 35.7 | 0.252 | | 0.164 | 0.101 | |
| Pouchitis | 68.0 | 39.0 | 0.039 | | 0.026 | 0.025 | 0.016 |
| PSC | 69.2 | 37.5 | 0.019 | | 0.012 | 0.010 | 0.0007 |
| Chronic Pouchitis | 78.6 | 42.3 | 0.025 | 4.7 (1.2~15.4) | 0.011 | 0.010 | 0.044 |
| N = 52 patients (only patients with pANCA information) | | | | | | | |
| Pouchitis | 65.2 | 37.9 | 0.079 | | 0.043 | 0.034 | |
| Chronic Pouchitis | 73.3 | 40.5 | 0.067 | 3.5 (0.092~13.7) | 0.024 | 0.020 | |
| N = 72 patients (52 patients with pANCA information) | | | | | | | |
| Pouchitis | 65.3 | 37.0 | 0.036 | | 0.043 | 0.034 | |
| Chronic Pouchitis | 75.0 | 39.3 | 0.022 | 4.4 (1.2~15.4) | 0.024 | 0.020 | |

*using only patients with severe but non-cancerous disease demonstrate that chronic pouchitis can develop by both pANCA-dependent and pANCA-independent pathways. These results further indicate that pANCA can be combined with the FA1 171 allele to produce a particularly sensitive method of predicting the development of pouchitis or chronic pouchitis.

All journal article, reference, and patent citations provided above, in parentheses or otherwise, whether previously stated or not, are incorporated herein by reference.

Although the invention has been described with reference to the examples above, it should be under stood that various modifications can be made without departing from the spirit of the invention. Accordingly, the invention is limited only by the following claims.

We claim:

1. A method of determining a risk of pouchitis development following a surgical procedure whereby an internal pouch is created in a patient with ulcerative colitis, comprising determining the presence or absence in said patient of a pouchitis-associated allele linked to an interferon γ receptor locus,
   wherein the presence of said pouchitis-associated allele indicates an increased risk of pouchitis development.

2. The method of claim 1, wherein said interferon γ receptor locus is an interferon γ receptor 1 gene (IFNGR1).

3. The method of claim 2, wherein said pouchitis-associated allele is within said IFNGR1.

4. The method of claim 3, wherein said pouchitis-associated allele is located within the sixth intron of said IFNGR1.

5. The method of claim 4, wherein said pouchitis-associated allele is an IFNGR1 FA1 microsatellite.

6. The method of claim 5, wherein said pouchitis-associated allele is a FA1 microsatellite 171 allele.

7. The method of claim 6, wherein said surgical procedure comprises ileal pouch anal anastomosis.

8. The method of claim 1, wherein said pouchitis is chronic pouchitis.

9. A method of determining a risk of chronic pouchitis development following ileal pouch anal anastomosis in a patient with ulcerative colitis, comprising determining the presence or absence in said patient of an interferon γ receptor 1 FA1 microsatellite 171 allele,
   wherein the presence of said 171 allele indicates an increased risk of chronic pouchitis development.

10. The method of claim 1, wherein determining the presence or absence of said pouchitis-associated allele comprises enzymatic amplification of nucleic acid from said patient.

11. The method of claim 1, further comprising a step selected from the group consisting of electrophoretic analysis, restriction fragment length polymorphism analysis, sequence analysis, and any combination thereof.

12. The method of claim 1, wherein said pouchitis-associated allele is associated with chronic pouchitis with an odds ratio of at least 4 and a lower 95% confidence limit greater than 1.

13. The method of claim 6, wherein the presence or absence of a FA1 microsatellite 171 allele is determined, comprising:

(a) obtaining material from said patient comprising nucleic acid comprising the FA1 microsatellite locus of interferon γ receptor 1 gene; and
(b) enzymatically amplifying said nucleic acid to produce an amplified fragment comprising said FA1 microsatellite locus,
  wherein the presence of the FA1 microsatellite 171 allele indicates an increased risk of pouchitis development.

14. The method of claim 13, further comprising:
(c) electrophoresing said amplified fragment, thereby determining whether a FA1 microsatellite 171 allele is present.

15. The method of claim 1, wherein said pouchitis-associated allele is linked to an IFNGR1 FA1 microsatellite 171 allele.

* * * * *